United States Patent [19]
Beavers

[11] Patent Number: 5,856,527
[45] Date of Patent: Jan. 5, 1999

[54] PREPARATION OF 3-ALKYLTETRAHYDROFURANS

[75] Inventor: William Anthony Beavers, Longview, Tex.

[73] Assignee: Eastman Chemical Company, Kingsport, Tenn.

[21] Appl. No.: 944,853

[22] Filed: Oct. 6, 1997

Related U.S. Application Data

[60] Provisional application No. 60/028,980 Oct. 21, 1996.
[51] Int. Cl.$^6$ .................................................. C07D 307/06
[52] U.S. Cl. ............................................................. 549/429
[58] Field of Search .............................................. 549/429

[56] References Cited

U.S. PATENT DOCUMENTS

| | | | |
|---|---|---|---|
| 4,590,285 | 5/1986 | Ernst | 549/429 |
| 4,859,801 | 8/1989 | Ernst | 549/509 |
| 4,879,420 | 11/1989 | Ernst | 568/617 |
| 5,536,854 | 7/1996 | Weyer et al. | 549/508 |

FOREIGN PATENT DOCUMENTS

| | | |
|---|---|---|
| 0 340 970 | 11/1989 | European Pat. Off. |
| 0 343 841 | 11/1989 | European Pat. Off. |
| 96-291158 | 11/1996 | Japan |

OTHER PUBLICATIONS

Zenk et al., Synthesis, 695 (1984).
Botteghi et al., J. Org. Chem., 37, 1835 (1972).
Talipov et al., Zh. Org. Khim., 29, 1024 (1993).
Shriner et al., Org. Synth. Coll. vol. IV, 786 (1963).
Comprehensive Organic Synthesis, B. M. Trost, Ed., Pergamon Press, New York, vol. 2, 612 (1991).
Starr et al., Org. Synth. Coll. vol. II, 566 (1943).
Chemical Abstracts, vol. 120, No. 17, 25 Apr. '94, Talipov, et al.

*Primary Examiner*—Bernard Dentz
*Attorney, Agent, or Firm*—Michael J. Blake; Harry J. Gwinnell

[57] ABSTRACT

Disclosed is a process for the preparation of 3-alkyltetrahydrofurans by a two-step process wherein 2,3-dihydrofuran is reacted with an acetal to form an intermediate compound which may be converted to a 3-alkyltetrahydrofuran by contacting the intermediate with hydrogen in the presence of a catalytic amount of a Group VIII noble metal or rhenium, water and a strong acid.

9 Claims, No Drawings

PREPARATION OF 3-ALKYLTETRAHYDROFURANS

This application claims the benefit of U.S. Provisional Application No. 60/028,980, filed Oct. 21, 1996.

This invention pertains to a process for the preparation of 3-alkyltetrahydrofurans. More specifically, this invention pertains to a two-step process wherein 2,3-dihydrofuran is converted to 3-alkyltetrahydrofurans. The 3-alkyltetrahydrofurans produced in accordance with the present invention are useful as industrial solvents and as monomers in the manufacture of polymers such as elastomers.

Alkyltetrahydrofurans, or precursors which may be cyclized to alkyltetrahydrofurans, may be prepared by a number of procedures. For example, Zenk et al., *Synthesis*, 695 (1984), describe a process for alkylating γ-butyrolactone with alkyl halides to produce β-alkyl-γ-butyrolactones which may be hydrogenolyzed to 3-alkyl-tetrahydrofurans. Botteghi et al., *J. Org. Chem.*, 37, 1835 (1972), describe procedures for the preparation of 4-alkyl-2,3-dihydrofurans wherein allyl alcohols and acrolein derivatives are hydroformylated and the intermediates are dehydrated or dealcoholated to prepare 4-alkyl-2,3-dihydrofurans. Another more efficient method for preparing such 3-alkyltetrahydrofuran precursors is described by Talipov et al., *Zh. Org. Khim.*, 29, 1024 (1993), comprises the reaction of formaldehyde with 1-alkenes in a Prins reaction in trifluoroacetic acid to give 3- and 4-alkyldihydrofurans in modest yields. In this method, two carbon atoms from the 1-alkene become incorporated into the dihydrofuran ring leaving an alkyl substituent in the 3- or 4-position two carbon atoms smaller than the starting 1-alkene. Talipov et al., however, reported success only with 1-alkenes at least as large as 1-hexene, i.e., the alkyl substituent of the alkyldihydrofuran contain at least 4 carbon atoms. Furthermore, there are, apparently, a number of directions the Talipov et al. reaction can take. For example, Shriner et al., *Org. Synth. Coll. Vol. IV*, 786 (1963) report good yields of 1,3-dioxanes starting with formaldehyde and other 1-alkenes (styrenes).

The prior art also discloses a number of methods for preparing 3-methyltetrahydrofuran, a compound which is not obtained from the process of the present invention. Some, but not all, of these methods may be extended to the preparation of other 3-alkyltetrahydrofurans wherein the alkyl group contains 2 or more carbon atoms. One method, described by Abe et al., in Japanese Published Patent Application JP 96-291,158, comprises the oxidative dicarboxylation of propylene to 2-methylsuccinic acid esters which then is reduced to the corresponding butanediol which is cyclized to 3-methyltetrahydrofuran. Starting with any 1-alkene larger than propylene would give 3-alkyltetrahydrofuran products wherein the alkyl group is larger than methyl.

Ernst, in U.S. Pat. No. 4,879,420, discloses a process for preparing 3-methyltetrahydrofuran in which 4-hydroxybutyraldehyde is reductively alkylated with formaldehyde to give 2-methyl-1,4-butanediol which is cyclized into 3-methyltetrahydrofuran. The substitution of an aldehyde containing 2 or more carbon atoms would give 3-alkyltetrahydrofurans in which the alkyl substituent would contain 2 or more carbon atoms. However, the use of an aldehyde bearing hydrogen(s) on the α-carbon atom would give crossed aldol condensations, thereby lowering the yield of the desired 3-alkyltetrahydrofuran. Only aldehydes such as benzaldehyde or pivalaldehyde having no hydrogen atoms on their α-carbon atom would avoid this disadvantageous side reaction.

It is known that vinyl ethers (also enol ethers) react with a number of compounds under Lewis acid catalysis. See, for example, *Comprehensive Organic Synthesis*, B. M. Trost, Ed., Pergamon Press, New York Vol. 2, 612 (1991).

The present invention provides a process for the preparation of a 3-alkyltetrahydrofuran having the formula

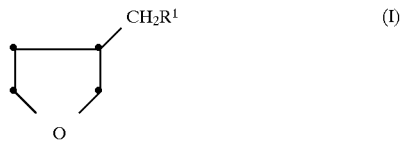

which comprises the steps of:
(1) contacting 2,3-dihydrofuran with an acetal having the formula

in the presence of an acidic catalyst to produce an intermediate compound having the formula

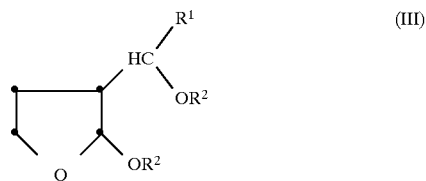

and
(2) contacting the intermediate compound from step (1) with hydrogen in the presence of a catalytic amount of a Group VIII noble metal or rhenium, water and a strong acid; wherein $R^1$ is an aliphatic, cycloaliphatic, aromatic or heterocyclic radical and each $R^2$ is an alkyl radical.

The acidic material useful for catalyzing the first step of the process may be selected from various Bronsted or Lewis acids. Examples of such Lewis acids include aluminum trichloride, aluminum tribromide, aluminum trifluoride, aluminum triiodide, boron trifluoride, boron trichloride, boron tribromide, boron triiodide, iron (III) chloride, iron (III) bromide, iron (III) fluoride, iron (III) iodide, tin (IV) chloride, tin (IV) bromide, tin (IV) fluoride, tin (IV) iodide, zinc fluoride, zinc chloride, zinc bromide, zinc iodide, titanium (IV) fluoride, titanium (IV) chloride, titanium (IV) bromide, titanium (IV) iodide, zirconium tetrachloride, zirconium tetrabromide, zirconium tetrafluoride, and zirconium tetraiodide. Examples of the Bronsted acids include sulfuric acid, nitric acid, hydrogen chloride, hydrogen bromide, hydrogen iodide, hydrogen fluoride, phosphoric acid, trifluoroacetic acid, and toluenesulfonic acid. Because of its high activity and its liquid form, the most preferred catalyst is boron trifluoride introduced as its diethyl etherate complex.

The concentration of the acidic catalyst used in the process can be varied significantly depending, for example, on the particular catalyst used although only low concentrations usually are needed. By adjusting the reaction conditions, any concentration from 0.1 ppm to 99 percent for liquid or saturation for solid catalysts, based on the weight of the step (1) reaction mixture, may be used. Preferred concentrations range from 1 ppm to 10 weight percent (same basis). The preferred catalyst, boron trifluoride, preferably is used in a concentration within the range of about 10 to 3000 ppm, most preferably within the range of about 500 to 1500 ppm.

Step (1) of the process may be carried out over a wide range of temperatures, e.g., from −50° to 200° C., although the use of temperatures in the range of about −20° to 50° C. normally are preferred. The most preferred temperature range is about −10° C. to 20° C. The use of temperatures below the preferred temperature ranges results in slow reaction rates which necessitates the use of excessive reaction times. The use of temperatures above the preferred temperature ranges may cause catalytic cracking of acetal (II), leading to the formation of excessive amounts of byproducts.

To minimize by-product formation, the mole ratio of the acetal to 2,3-dihydrofuran should be in the range of 1:1 to 100:1. Because of material handling costs and the energy required to separate and recycle the unused acetal, the most practical acetal:2,3-dihydrofuran mole ratio is 3:1 to 10:1. The first step of the process is carried out under substantially anhydrous conditions. Although not essential, inert (nonreactive) solvents such as aliphatic and aromatic hydrocarbons, ethers and halogenated hydrocarbons may be employed in the first step.

The desired product in step (1), compound (III), is a 1:1 adduct of 2,3-dihydrofuran and acetal (II). Since compound (III) is itself an acetal, it also can add 2,3-dihydrofuran to form the 2:1 adduct (several isomers, each of which is also an acetal). This condensation with additional 2,3-dihydrofurans can repeat until the product mixture contains each of 1:1, 2:1, 3:1, 4:1, etc. adducts of 2,3-dihydrofuran and acetal (II). It is apparent that each additional condensation beyond the 1:1 adduct stage lowers the yield of the desired 1:1 adduct product. Other factors may lower the yield of the 1:1 adduct based on the 2,3-dihydrofuran fed, but this method is an important one. Therefore, reaction conditions are chosen to optimize the production of the 1:1 adduct of 2,3-dihydrofuran and acetal and minimize formation of all other adduct/by-products.

One important determinant of the yield of compound (III), the 1:1 adduct of 2,3-dihydrofuran and acetal (II), is the catalyst concentration. Before adding any 2,3-dihydrofuran, essentially all of the catalyst exists as a catalyst/acetal (II) complex. Upon adding the first increment of 2,3-dihydrofuran, the reaction initially produces a catalyst/1:1 adduct complex. This complex reacts either with acetal (II) to reform a catalyst/acetal (II) complex and free 1:1 adduct (a chain transfer step in polymerization terminology) or it reacts with additional 2,3-dihydrofuran to form a catalyst/2:1 adduct complex (a chain propagation step in polymerization terminology). Even though the degree of polymerization always remains low in the process of the present invention, this reaction actually is the first stage of a polymerization and the competition between the chain transfer step and the chain propagation step determines the amount of higher adducts formed and, inversely, the yield of the 1:1 adducts.

When using catalyst concentrations below the preferred catalyst concentration ranges, the catalyst is the limiting reagent permitting an accumulation of unreacted 2,3-dihydrofuran. When the catalyst/1:1 adduct complex (from the reaction of the catalyst/acetal complex and 2,3-dihydrofuran) contacts unreacted 2,3-dihydrofuran, it forms some catalyst/2:1 adduct complex thereby lowering the yield of the 1:1 adduct. When operating within the preferred catalyst concentration ranges, the 2,3-dihydrofuran becomes the limiting reagent so that the catalyst/1:1 adduct complex (from the reaction of the catalyst/acetal complex and 2,3-dihydrofuran) contacts essentially no unreacted 2,3-dihydrofuran. Therefore, it forms almost no catalyst/2:1 adduct complex and resulting in high yields of the 1:1 adduct. Almost all of the catalyst/1:1 complex has time to exchange with acetal (II) to form fresh catalyst/acetal (II) complex and free 1:1 adduct. The next increment of 2,3-dihydrofuran added encounters the catalyst/acetal (II) complex almost exclusively so that all it can do is make more 1:1 adduct with acetal (II).

When using catalyst concentrations higher than the preferred catalyst concentration ranges, another mechanism causes lower 1:1 adduct yields. The use of such higher catalyst concentrations promotes the cracking of acetal (II) into an alcohol and a vinyl ether. Since 2,3-dihydrofuran itself is a vinyl ether derivative, the vinyl ether from the cracking of acetal (II) undergoes the same reactions as 2,3-dihydrofuran. Moreover, the alcohol from the acetal cracking also can add to 2,3-dihydrofuran to form a 2-alkoxytetrahydrofuran by-product. Consequently, the yield of the desired product falls because both the acetal (II) and 2,3-dihydrofuran reactants form products other than their 1:1 adduct.

In the second step of the process, intermediate compound of formula (III) is converted to a 3-alkyltetrahydrofuran by the hydrogenolysis of all the alkoxy groups while not affecting the tetrahydrofuran ring. The hydrogenolysis is carried out by contacting intermediate compound (III) with hydrogen in the presence of a catalytic amount of a Group VIII noble metal, water and a strong acid under hydrogenolysis conditions of temperature and hydrogen pressure.

Examples of the catalytic metals which may be employed in the second step of my novel process include palladium, platinum, rhodium, rhenium, ruthenium, iridium, etc. The Group VIII noble metal catalyst preferably is rhodium, iridium or, especially, palladium. The form of the Group VIII nobel or rhenium metal catalyst is not critical although the most efficient use of the expensive metals is in a finely divided form on an appropriate support. Normally, supported catalysts comprise about 0.1 to 10 weight percent Group VIII noble or rhenium metal deposited on a suitable catalyst support material such as activated charcoal, silica, alumina, titania, zirconia, barium sulfate, and calcium sulfate. Alternatively, the catalyst metals may be used as finely divided, unsupported metals, e.g., palladium black, although this mode of catalyst utilization may not represent the most efficient use of the expensive Group VIII noble metal. It also is possible to use compounds of the Group VIII noble metals or rhenium, e.g., salts such the chloride, fluoride, bromide, nitrate, carboxylate, e.g., acetate or benzoate; oxides;, or hydroxides may be used. In addition to soluble salts of Group VIII noble metals and rhenium, insoluble salts such as the phosphates, sulfates, or iodides can be used.

The concentration of the Group VIII noble or rhenium metal which is catalytically effective varies significantly depending, for example, upon the particular metal utilized, the form in which the metal is used and other process variables such as temperature, pressure and residence time. For example, the amount of catalytic metal present may be from 0.000001 to more than 100 percent based on the g-atoms of Group VIII noble or rhenium metal per g-mole of intermediate compound (III) present. The amount of Group VIII noble or rhenium metal present preferably is about 0.00001 to 0.2, most preferably 0.001 to 0.1, g-atoms Group VIII noble metal or rhenium per mole of intermediate compound (III) present.

Examples of the strong acids which may be used in the second step of the process include sulfuric, phosphoric, nitric, hydrofluoric, hydrochloric, hydrobromic, hydriodic, trifluoroacetic, or a sulfonic acid such as alkanesulfonic acids, arylsulfonic acids, e.g., toluenesulfonic acid, and polymeric sulfonic acids, e.g., acidic ion exchange resins comprising styrene/divinylbenzete polymers bearing sulfo groups. The concentration of the strong acid may be in the range of 0.000001 molar to 15 molar although concentrations of 0.001 molar to 5 are preferred and concentrations of 0.01 to 1 molar are most preferred. When using the preferred amounts of palladium and strong acid, the mole ratio of palladium to strong acid is in the range of about 1:10 to 1:100.

In certain modes of operation, the strong acid may be utilized in the form of a catalyst support material impregnated with at least one non-volatile (or low volatile) strong acid, e.g., sulfuric and phosphoric acid. Alumina, titania, zirconia, barium sulfate, calcium sulfate and silica containing about 0.0001 to 50 weight percent, based on the total weight of the supported catalyst, sulfuric or phosphoric acid are examples of such supported, strong acids. Alternatively, the strong acid may be an acidic, ion exchange resin comprising a polymer bearing sulfonic acid groups. Also, since compound (III) often is not completely converted into gaseous (at the reaction temperatures) compound (I), supplemental non-volatile acid must be periodically reintroduced onto the catalyst support to maintain the catalyst activity.

The second step of the present process may be carried out in the presence of iodine or an iodine compound such as an iodide salt. The inclusion of iodine or and iodine compound as a promoter in step (2) of the process permits the use of lower reaction temperatures. Depending on the concentration of the optional iodine promoter concentration, the hydrogenolysis temperature can be up to 60° C. lower than the temperature without the iodine promoter. However, iodine is a hydrogenolysis catalyst inhibitor so that the required amount of metal catalyst normally must be increased by up to 200 to 1000 percent to counteract this inhibiting effect. Use of an iodine promoter depends on the sensitivity of the product yield to lower temperatures. When the use of iodine or an iodine compound can be justified, the amount of iodine or iodine compound present in the step (2) reaction mixture may range from 0.000001 molar to 10 molar. However, iodine concentrations in the range of about 0.0001 molar to 1 molar are preferred with concentrations in the range of 0.001 molar to 0.1 molar being most preferred.

The second step of the process of the present invention can be achieved through the utilization of at least 3 basic modes of operation: (1) a single, convenient hydrogenolysis reaction removing all alkoxy side groups simultaneously (as described hereinabove); (2) a sequential hydrogenolysis removing one easily-hydrogenolyzed alkoxy group before the other; and (3) a dealcoholysis removing all alkoxide groups as their corresponding alcohols followed by hydrogenation. In each of the three modes of operation (or embodiments of the second step), the intermediate compound of formula (III), the 1:1 adduct, is converted into 3-alkyltetrahydrofuran, compound (I), by the replacement of all of the alkoxy groups with hydrogen while not affecting the tetrahydrofuran ring. The same catalyst system can be used in all 3 modes of operation, adjusting the severity of the conditions and the ratios of the components to change the hydrogenolytic potentials. The second and third modes of operation are step-wise or sequential embodiments or variations of the first mode of operation and are encompassed by the definition of step (2) set forth hereinabove.

In the first mode of operation, the simultaneous hydrogenolytic removal of all side alkoxy groups is carried out by contacting the intermediate compound (III) with hydrogen in the presence of a catalytic amount of a Group VIII noble metal-containing hydrogenation catalyst, a strong acid, water, and, optionally, an iodine promoter under hydrogenolysis conditions of temperature and pressure. This treatment causes the preferential removal of the alkoxy side groups while leaving the tetrahydrofuran ring largely intact. During this simultaneous hydrogenolysis, the various stages of the reaction with the accompanying intermediate products may be observed by slowing down or interrupting the reaction at various times of its progression. Alternatively, the overall yield of product (I) can be enhanced by separating the reaction into these stages by progressively increasing the severity of the hydrogenolysis conditions recovering whatever product (I) is produced at each stage and providing the rationale for the second case.

In the second mode of operation [second embodiment of step (2)], each alkoxy group is removed with a selective hydrogenolysis. Thus, treating compound (III) with hydrogen in the presence of catalytic amounts of a Group VIII noble metal, water, and a strong mineral acid (like the first mode catalyst system except for the absence of the optional iodine promoter) at moderate temperatures selectively removes the 2-alkoxy group while producing compound (I) in moderate yields. It is believed that this selective hydrogenolysis takes place by hydrolysis of the compound (III) acetal group producing 4-hydroxy-2-(1-alkoxyalkyl)-butanal which undergoes hydrogenation or hydrogenolysis producing compound (I) and 3-(1alkoxyalkyl) tetrahydrofuran. The other products are the two isomers of 3-(1-alkoxyalkyl)-tetrahydrofuran having the formula

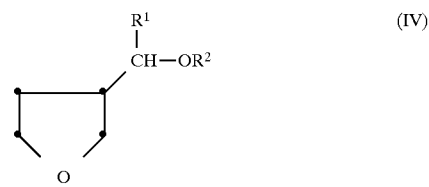

and the combined yield of these three products is nearly quantitative. Removing the alkoxy side group from compound (IV) requires more severe hydrogenolysis conditions of temperature, acidity, and pressure, but the beneficial effect of water no longer exists so the reaction can take place in the presence of a large variety of hydrogenolysis catalysts which are adversely affected by water. Thus, hydrogenolysis of compounds (IV) in the presence of a catalytic amount of a Group VIII nobel metal catalyst, a strong mineral acid, and an optional iodine or iodine compound promoter (like the catalyst system for the first mode of operation except for the absence of water) at higher temperatures than the first treatment of compound (III) will remove the side alkoxy group to form compound (I) in moderate to good yields. Alternatively and since water is no longer a necessary part of the reaction mixture, hydrogenolysis of compounds (IV) in the presence of a catalytic amount of a Group VIII noble metal catalyst can take place on a highly acidic and water-sensitive solid acid such as alumina or titania (like the first mode catalyst system except for the absence of water and the solid acid taking the place of the mineral acid and the iodine) at higher temperatures than the first treatment of compound (III) to remove the alkoxy side group from compounds (IV) to form compound (I) in good to moderate yields. The primary advantage to this inconvenient, sequential side group removal is the improved overall yield of compound (I) achievable by not subjecting the vulnerable tetrahydrofuran ring to unnecessarily severe hydrogenolysis conditions.

In a third mode of operation, all of the side alkoxy groups are removed separately from the hydrogenation by passing compound (III) over an acidic catalyst causing its cleavage into a 3-alkylfuran having the formula

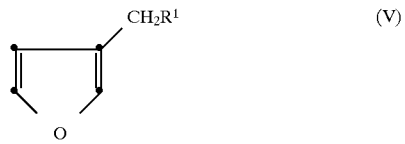

and one or more alcohols. The 3-alkylfuran may be hydrogenated to the corresponding 3-alkyltetrahydrofuran in high yields by known procedures, e.g., the procedure described by Starr et al., Org. Synth. Coll. Vol. II, 566 (1943). With the high activity of the furan ring, this mode of operation produces a large number/quantity of by-products and therefore does not give optimum yields of compound (I).

The temperatures under which step (2) is performed depends upon the particular mode of operation used. The temperature range for the first mode of carrying out step (2) (simultaneous hydrogenolysis of all side alkoxy groups) is about 50° to 450° C. with about 150° to 350° C. being preferred and about 200° to 300° C. being most preferred. With iodine present as an optional promoter, the most preferred temperature range falls to about 140° to 240° C. When using the second mode of operation (sequential hydrogenolysis of the alkoxy side groups), the temperature range for the removal of the first alkoxy side group is about 0° to 250° C. with about 50° to 200° C. being preferred and about 70° to 180° C. being most preferred. For the removal of the second alkoxy group, the temperature range is about 150° to 400° C. with about 200° to 350° C. being preferred and about 220° to 330° C. being most preferred. When using the third mode of operation (dealcoholysis/hydrogenation), the temperature range for the dealcoholysis is about 20° C. to 400° C. with about 50° to 350° C. being preferred and about 80° to 300° C. being most preferred. For the hydrogenation of the resulting furan (V), the temperature range is about 0° to 200° C. with about 50° to 150° C. being preferred, and about 60° to 140° C. being most preferred.

The hydrogen pressures utilized in step (2) of the process (regardless of the mode of operation) are not critical and may range, for example, from 0.1 to 1000 bars absolute although hydrogen pressures in the range of about 2 to 500 bars absolute, especially about 10 to 100 bars absolute are preferred. The use of an inert solvent such as water, alkanes and halogenated hydrocarbons is optional, but not essential, in the second step.

The aliphatic, cycloaliphatic, aromatic or heterocyclic radical which $R^1$ may represent and the alkyl radical which each $R^2$ may represent are not critical and may contain up to about 12 carbon atoms. Examples of such groups include methyl, ethyl, propyl, butyl. isobutyl, hexyl, octyl, 2-ethylhexyl, decyl, dodecyl, benzyl, phenethyl, cyclopentyl, cyclohexyl, methylcyclohexyl, cycloheptyl, phenyl and phenyl substituted with lower alkyl, lower alkoxy or halogen. $R^1$ and each $R^2$ preferably are independently selected from alkyl, e.g., alkyl of up to about 8 carbon atoms, most preferably lower alkyl, i.e., alkyl of up to about 4 carbon atoms.

The process of the present invention is further illustrated by the following examples.

EXAMPLE 1

The equipment used in this example was a 500 mL, round-bottom flask containing an overhead stirrer, an addition funnel, a thermowell with thermometer, a side arm capped with a septum cap, and a reflux condenser topped with a nitrogen inlet through which a dry nitrogen blanket was introduced throughout the duration of the reaction. After flame drying all equipment, the charge to the round bottom flask was 250 mL of anhydrous acetal (acetaldehyde diethyl acetal, d=0.8314, 208 g, 1.759 moles, dried by distillation from calcium hydride). The charge to the addition funnel was 80 mL of anhydrous acetal (67 g, 0.563 mole) and 55 mL of anhydrous 2,3-dihydrofuran (d=0.927, 51 g, 0.727 mole, dried by distillation from calcium hydride,). The molar ratio of the total acetal used to the 2,3-dihydrofuran was 3.19.

After stirring and cooling the contents of the round bottom flask to 5° C., 0.14 milliliters of boron trifluoride etherate (d =1.154, 0.12 g, 0.81 millimoles) were added through the septum cap to give a boron trifluoride concentration in the reaction pot of 237 ppm. The addition of the contents of the addition funnel to the stirred contents of the round bottom flask required 160 minutes while maintaining a temperature of about 5° to 15° C. throughout this addition. Stirring another 15 minutes after completing the addition ensured complete consumption of the 2,3-dihydrofuran. Gas chromatographic (GC) analysis of the contents of the flask at this point showed a 99.8% conversion of the 2,3-dihydrofuran. The yield of 2-ethoxy-3-(1-ethoxyethyl) tetrahydrofuran, the 1:1 adduct (4 isomers) was 84.4%. All of the yields reported herein are area percent yields determined by GC analyses of the reaction mixture at the conclusion of the experiment. The product also contained 2-(2-ethoxytetrahydrofuran-3-yl)-3-(1-ethoxyethyl) tetrahydrofuran, the 2:1 adduct (16 isomers), in 13.2% yield, and 2-(2-ethoxytetrahydrofuran-3-yl)-3-(3-(1-ethoxyethyl)-tetrahydrofuran-2-yl)-tetrahydrofuran, the 3:1 adduct (64 isomers), in 0.9% yield. The boiling point of the isolated 1:1 adduct was 91°–94° C./18 mm Hg.

EXAMPLE 2

Example 1 was repeated using a molar ratio of acetal to 2,3-dihydrofuran of 3.24, an addition time of 130 minutes, a boron trifluoride catalyst concentration of 223 ppm, and a reaction temperature of 40° to 55° C. The yield of 2-ethoxy-3-(1-ethoxyethyl)-tetrahydrofuran, the 1:1 adduct, was 80.0%. The yield of the 2:1 adduct was 10.3 percent and the yield of the 3:1 adduct was 1.6%. The remainder of the material balance was oligomers of acetal, 5.0%, and 2-ethoxytetrahydrofuran, 3.1%.

EXAMPLE 3

Example 1 was repeated except the mole ratio of the acetal to the 2,3-dihydrofuran was 3.35, the overhead stirrer was replaced by a magnetic stirring bar, the catalyst concentration was 103 ppm boron trifluoride; and the reaction temperature was 3° to 7° C. with an addition time of 60 minutes. The yield of the 1:1 adduct was 67.9%, the yield of the 2:1 adduct was 22.5%; and, the yield of the 3:1 adduct was 4.0%.

EXAMPLE 4

Example 1 was repeated using a mole ratio of acetal to 2,3-dihydrofuran of 3.62, a catalyst concentration of 106 ppm and a reaction temperature of −2° to 5° C. with an addition time of 245 minutes. The yield of the 1:1 adduct was 68.7%; the yield of the 2:1 adduct was 24.0%; and the yield of the 3:1 adduct was 5.2%. In addition, there was detected 2-((2-ethoxytetrahydrofuran-3-yl)-tetrahydrofuran-3-yl)-3-(3-(1-ethoxyethyl)tetrahydrofuran-2-yl)-tetrahydrofuran, the 4:1 adduct of 2,3-dihydrofuran and acetal, in a yield of 0.1%.

When compared to the results obtained in Example 2, the results achieved in this example show that the effect of improved stirring efficiency and longer reagent addition times was negligible.

EXAMPLE 5

Example 1 was repeated except that the reaction pot was a 5000 mL round bottom flask. The mole ratio of the acetal to the 2,3-dihydrofuran was 3.52, the boron trifluoride catalyst concentration was 43 ppm, and the reagent addition time was 200 minutes. The yield of the 1:1 adduct was 66.5%; the yield of the 2:1 adduct was 25.9%; the yield of the 3:1 adduct was 5.8%; and, the yield of the 4:1 adduct was 0.5%.

EXAMPLE 6

Example 4 was repeated using recycled acetal as the acetal reagent and a different means of dehydrating the apparatus and the reagent. In this case, the acetal from prior experiments, flash distilled from a basified distillation pot, containing acetal and a few lower boiling impurities was fractionally distilled until the temperature in the distillation head reached 101° C. At this point, the distillation ceased and a reflux began separating any water condensing in the reflux head with a Dean-Starke trap. Within 6 hours after the removal of the last of the water, the reflux was interrupted and the flask contents were allowed to cool to room temperature. At this point, analysis of the flask contents showed a water content less than 10 ppm.

From this point the reaction continued as usual using a reaction temperature of 8° to 13° C., an acetal to 2,3-dihydrofuran molar ratio of 3.62, a boron trifluoride concentration of 35 ppm, and a reagent addition time of 145 minutes. The workup was changed to remove the boron trifluoride catalyst, keeping it from harming the acetal/2,3-dihydrofuran adducts. In this modification, after completion of the addition of all condensing reagents and allowing an additional 30 minutes for all reagents to react, sufficient 20% methanolic sodium hydroxide was added slowly at this point to equal three molar equivalents of the boron trifluoride catalyst. The unreacted acetal and other low boiling components were removed by a fractional distillation at 150 mm Hg until the base temperature reached 120° C. The distillate containing acetal, methanol, and other low boiling components was collected for recycling to other preparations. The base material was cooled to room temperature and suction filtered through a compressed glass wool filter to remove the precipitated salts. The filtrate was returned to the distillation flask for continued fractional distillation and the filter cake was discarded. After a small forerun of more acetal which was combined with the batch for recycle, the 1:1 adduct product distilled at 74° to 78° C./7 mm Hg. The 2:1 adduct product also distilled at 125° to 138° C./7 mm Hg. Gas chromatographic analysis of each of these fractions showed purities of 95+ percent to a mixture of the 4 stereoisomers of the 1:1 adduct and 12 of the 16 possible stereoisomers of the 2:1 adduct.

The product yield determined by gas chromatography was 63.2% of the 1:1 adduct compared with an isolated yield of 61.3%. The yield of the 2:1 adduct was 25.8% by gas chromatography compared with an isolated yield of 22.9%. This experiment demonstrates the feasibility of using recycled acetal and a catalyst removal procedure, both of which may be used in a commercial process.

EXAMPLE 7

Example 5 was repeated using an acetal to 2,3-dihydrofuran molar ratio of 3.21, a reaction temperature of −6° to −2° C., a catalyst concentration of 1018 ppm, and a reagent addition time of 175 minutes. Gas chromatographic analysis of the reaction mixture showed a 91.2% yield of the 1:1 adduct, a 7.1% yield of the 2:1 adduct, and a 0.2% yield of the 3:1 adduct.

EXAMPLE 8

Example 5 was repeated using an acetal to 2,3-dihydrofuran molar ratio of 3.48, a reaction temperature of −9° to −6° C., a catalyst concentration of 2125 ppm, and a reagent addition time of 165 minutes. Gas chromatographic analysis of the reaction product showed an 84.3% yield of the 1:1 adduct, a 5.0% yield of the 2:1 adduct, a 0.1% yield of the 3:1 adduct, a 6.5% yield of 1,1,3-triethoxybutane, a 0.1% yield of 1,1,3,5-tetraethoxyhexane, and a 3.8% yield of 2-ethoxytetrahydrofuran.

EXAMPLES 9–13

The procedures utilized in the preceding examples were repeated in the performance of the experiments constituting Examples 9–13 wherein acetal was reacted with 2,3-dihydrofuran (DHF) using a variety of acetal:DHF mole ratios, temperatures, addition times and concentrations of boron trifluoride catalyst. The conditions used and results obtained are set forth in Tables I and II wherein Temp is the temperature in ° C. at which each reaction was carried out, Addn Time is the time in hours during which acetal was added from the addition funnel and Cat Conc is the amount of boron trifluoride present in the reaction mixture at the commencement of each reaction. In Table II, in which the amounts of products obtained in each experiment are reported, Adct means adduct, TEB is 1,1,3-triethoxybutane, TEH is 1,1,3,5-tetraethoxyhexane and ETHF is 2-ethoxytetrahydrofuran.

TABLE I

| Example No. | Acetal:DHF Mole Ratio | Temp | Addn Time | Cat Conc |
| --- | --- | --- | --- | --- |
| 9 | 1:3.50 | 64 to 68 | 2.0 | 219 |
| 10 | 1:3.35 | 4 to 12 | 2.6 | 39 |
| 11 | 1:3.19 | −2 to 2 | 2.6 | 34 |
| 12 | 1:3.49 | −3 to 2 | 2.4 | 664 |
| 13 | 1:5.34 | −6 to −2 | 2.0 | 1087 |

TABLE II

| Example No. | 1:1 Adct | 2:1 Adct | 3:1 Adct | 4:1 Adct | TEB | TEH | ETHF |
| --- | --- | --- | --- | --- | --- | --- | --- |
| 9 | 51.2 | 4.8 | 0.1 | 0.0 | 19.4 | 2.3 | 15.3 |
| 10 | 59.0 | 26.3 | 8.7 | 3.3 | 1.2 | 0.0 | 1.2 |
| 11 | 64.0 | 27.8 | 5.0 | 0.5 | 1.3 | 0.0 | 1.1 |
| 12 | 87.8 | 8.8 | 0.5 | 0.0 | 1.7 | 0.0 | 1.0 |
| 13 | 91.2 | 7.1 | 0.2 | 0.0 | 0.9 | 0.0 | 0.6 |

EXAMPLES 14–17

These experiments utilized a tubular reactor consisting of a 30.5 cm (12 inch) section of 304 stainless steel tubing having an interior diameter of 9.5 mm (⅜ inch) and containing 10.0 g of 3–10 mesh (about 1–2 mm particles) diatomaceous earth impregnated with 12 weight percent phosphoric acid maintained in place with glass wool. A thermocouple was positioned in the middle of the catalyst bed to record reaction temperature. With a gas flow of 55 mL per minute, the reactor was heated in an oven to the required reactor temperature ±3° C. which was maintained throughout the reaction by a temperature controller. The reaction began by pumping 2-ethoxy-3-(1-ethoxyethyl)tetrahydrofuran (EEETHF) into the reactor at a rate of 10 mL per hour through a preheater to vaporize the sample. The vaporized material then was passed over the catalyst at the designated temperature. The effluent from the reactor flowed into a 50 mL round bottom flask containing anhydrous potassium carbonate to neutralize any acid eluting from the catalyst support and the flask was topped by a dry ice cooled trap to capture any volatile liquids exiting the reactor.

During the course of these de-alcoholization reactions, two events became apparent: (1) the acidic component of the catalyst eluted from the support necessitating its reintroduction as a part of the feedstock and (2) the catalyst gradually expanded with furan decomposition products as the reaction progressed, eventually completely plugging the reactor.

The results of these experiments are summarized in Table III below. The purpose of these experiments was to explore alternative routes to 3-alkyltetrahydrofurans, via hydrogenation of the furans in these examples. In Table III Temp is the temperature ±3° C. measured at the center of the catalyst bed, Cont Time is the contact time in seconds which the vaporized reactant was in contact with the phosphoric acid catalyst, Conv is mole percent conversion of the reactant EEETHF:

$$\frac{\text{Moles EEETHF Converted}}{\text{Moles EEETHF Fed}} \times 100$$

Product Selectivities for each reaction product is:

$$\frac{\text{Moles of Each Product}}{\text{Moles EEETHF Converted}} \times 100$$

EtFuran is 3-ethylfuran, MEEDHF means monoethoxyethyldihydrofurans, VDHF means vinyldihydrofurans and Heavies means higher molecular weight compounds.

TABLE III

| Example No. | Temp | Cont Time | Conv | EtFuran | MEEDHF | VDHF | Heavies |
|---|---|---|---|---|---|---|---|
| 14 | 80 | 7.3 | 91.5 | 63.9 | 3.4 | 1.4 | 30.2 |
| 15 | 121 | 6.6 | 99.6 | 59.8 | 4.7 | 2.1 | 30.7 |
| 16 | 161 | 6.0 | 99.9 | 61.3 | 3.9 | 2.2 | 30.4 |
| 17 | 198 | 5.5 | 99.9 | 61.5 | 3.9 | 2.4 | 30.5 |

EXAMPLE 18

The charge to a nitrogen flushed, 300 mL autoclave constructed of Hastelloy B alloy was 20 mL of 2-ethoxy-3-(1-ethoxyethyl)tetrahydrofuran (d=0.9204, 18 g, 98 millimoles), 1.0. g of iodine (3.94 millimoles), 0.50 mL of concentrated sulfuric acid (d=1.84, 0.92 g, 9.2 millimoles), 5 g of 5 weight percent palladium on activated charcoal, and 100 mL of distilled water. The autoclave was sealed and the contents thereof were stirred and heated at 220° C. under a hydrogen pressure of 35.5 bars absolute (500 psig) for 60 minutes. During this time, the pressure drop amounted to 13.4 bars absolute (180 psig). At the end of this time, gas chromatographic analysis showed the conversion of the starting material to be 99.8%. The yield to 3-ethyltetrahydrofuran was 59.6%. The remainder of the material balance consisted of a large number of compounds, none of which was formed in a selectivity greater than about 0.6%.

EXAMPLE 19

The procedure described in Example 18 was repeated except that the iodine was omitted and the hydrogenolysis was carried out at 300° C. over a period of 60 minutes. Gas chromatographic analysis showed the conversion of the starting material to be 100% with a selectivity to 3-ethyltetrahydrofuran of 38.7%.

EXAMPLE 20

Example 18 was repeated except the catalyst was replaced with 5 weight percent rhodium on activated charcoal and the hydrogenolysis was carried out at 220° C. for one hour at 35.5 bars hydrogen pressure. Gas chromatographic analysis of the reaction mixture showed a 100.0% conversion of the EEETHF starting material and a 3-ethyltetrahydrofuran yield of 61.2%.

EXAMPLE 21

Example 18 was repeated except the catalyst was replaced with 5 weight percent rhodium on alumina, the iodine was omitted and the hydrogenolysis was carried out at 120° C. for one hour at 35.5 bars of hydrogen pressure. Gas chromatographic analysis of the reaction mixture showed a 100.0% conversion of the starting material and a 3-ethyltetrahydrofuran yield of 45.1%.

EXAMPLE 22

Example 18 was repeated except the catalyst was replaced with 5 percent iridium on activated charcoal, the iodine was omitted and the hydrogenolysis was carried out at 180° C. for one hour at 35.5 bars hydrogen pressure. Gas chromatographic analysis of the reaction mixture showed a 100% conversion of the starting material and a 3-ethyltetrahydrofuran yield of 31.2%.

EXAMPLE 23

The charge to a nitrogen flushed, 2L Parr autoclave was 100 mL of 2-ethoxy-3-(1-ethoxyethyl)tetrahydrofuran (d=0.9402, 94 grams, 0.49 moles), 900 mL of distilled water, 6.5 mL of 85 weight percent phosphoric acid (d=1.685, 9.3 g, 95 millimoles) and 7.22 grams of 5 weight percent palladium on activated charcoal. After sealing the autoclave head, the experiment began by stirring the contents rapidly and feeding hydrogen to a hydrogen pressure of 35.5 bars absolute, a pressure which was maintained throughout the reaction by periodic additions of supplemental hydrogen gas. Rapid stirring continued for 30 minutes at ambient temperature, then at 120° C. for 2 hours, and then at 160° C. for 2 hours. During this time, the total pressure uptake amounted to 15.6 bars. Gas chromatographic analysis of the reaction mixture showed a 65.3% yield of 3-ethyltetrahydrofuran; a 32.2% yield of 3-(1-ethoxyethyl)tetrahydrofuran (two isomers) which is the intermediate hydrogenolysis product, giving a combined yield of useful materials 97.5%.

In the workup of the product, the solid catalyst was removed by vacuum filtration of the reaction mixture through a Buechner funnel and the filtrate was steam distilled until 500 mL of distillate had been collected. This distillate contained over 98% of the 3-ethyltetrahydrofuran and 3-(1-ethoxyethyl)-tetrahydrofuran produced. The aqueous distillation residue still containing the phosphoric acid catalyst was suitable for recycling to another hydrogenolysis. The steam distillate separated into two phases. The lower aqueous phase still contained substantial organic values which were recoverable by returning it to another steam distillation. The upper, organic phase was separated, dried, and subjected to a careful fractional distillation. The fraction boiling at 114°–116° C. consisted of 98% pure 3-ethyltetrahydrofuran. The pot residue consisted of 96% pure 3-(1-ethoxyethyl)tetrahydrofuran and was suitable for converting to 3-ethyltetrahydrofuran.

EXAMPLE 24

The charge to a nitrogen flushed, 300 mL Hastelloy B alloy autoclave was 20 mL of the impure 3-(1-ethoxyethyl) tetrahydrofuran recovered in Example 23, 100 mL of heptane, and 1.03 grams of 5 weight percent palladium on alumina. After attaching the autoclave head, the experiment began by stirring and heating the autoclave contents to 290° C. for one hour at a hydrogen pressure of 35.5 bars. At the end of this time, gas chromatographic analysis showed that the conversion of the starting material was 22.8% and the selectivity to 3-ethyltetrahydrofuran was 51.7%. With the 65.3% yield of 3-ethyltetrahydrofuran achieved in Example 23, the overall yield of 3-ethyltetrahydrofuran through this two-stage hydrogenolysis is 81.9%.

EXAMPLE 25

The procedure of Example 24 was repeated using 7.52 g of 5 weight percent palladium on carbon, 1.50 g iodine, 1.69 g 85 weight percent phosphoric acid, 50 mL of 3-(1-ethoxyethyl)tetrahydrofuran, 50 mL water and 50 mL methanol, and a hydrogenation temperature, pressure and time of 230° C., 35.5 bars absolute and 1 hour, respectively. Gas chromatographic analysis showed that the conversion of the starting material was 78.2% and the selectivity to 3-ethyltetrahydrofuran was 65.4%.

EXAMPLES 26–35

The procedures described in Examples 18 and 23 were repeated using a variety of conditions and catalysts to produce both 3-ethyltetrahydrofuran (ETHF) and 3-(1-ethoxyethyl)tetrahydrofuran (EETHF). The catalyst systems employed were as follows:
Example 26: 13.04 g of 5 weight percent Pd on carbon, 1.0 mL concentrated sulfuric acid.
Example 27: 5.02 g of 1 weight percent Pd on carbon, 1.0 mL concentrated sulfuric acid.
Example 28: 5.01 g of 1 weight percent Pd on carbon, 1.0 mL of 85 weight percent phosphoric acid.
Examples 29–35: 5.01 g of 1 weight percent Pd on carbon, 1.0 mL 85 weight percent phosphoric acid.
Iodine (1.0 g) was used only in Example 26.
The mixtures of 2-ethoxy-3-(1-ethoxyethyl) tetrahydrofuran (EEETHF) and water used in the hydrogenolysis reactions were:
Example 26: 20 mL EEETHF, 100 mL water.
Examples 27–28: 100 mL EEETHF, 900 mL water.
Example 29: 150 mL EEETHF, 850 mL water.
Examples 30–35: 200 mL EEETHF, 800 mL water.
The hydrogenolysis reactions of Examples 26–35 were carried out at a hydrogen pressure of 35.5 bars absolute and at the following temperatures and reaction times:
Example 26: 180° C. for 1 hour.
Examples 27–30: 120° C. for 2 hours, 160° C. for 2 hours.
Example 31: 110° C. for 2 hours, 150° C. for 2 hours.
Example 32: 100° C. for 2 hours, 140° C. for 2 hours.
Examples 33–35: 90° C. for 4 hours, 130° C. for 2 hours.
The results obtained in Examples 26–35 are reported in Table IV wherein the values given are selectivities to 3-(1-ethoxyethyl)tetrahydrofuran (EEETHF), 3-ethyltetrahydrofuran (ETHF) and Heavies (high molecular weight compounds). The conversion of the EEETHF reactant was 99.9% in Example 26 and 100% in Examples 27–35.

TABLE IV

| Example No. | Selectivities | | |
|---|---|---|---|
| | EEETHF | ETHF | Heavies |
| 26 | 38.8 | 50.4 | 1.0 |
| 27 | 52.6 | 33.0 | 0.8 |
| 28 | 60.9 | 37.1 | 0.2 |
| 29 | 61.3 | 37.5 | 0.2 |
| 30 | 60.3 | 38.8 | 0.0 |
| 31 | 57.0 | 39.9 | 0.8 |
| 32 | 52.7 | 44.2 | 0.6 |
| 33 | 57.9 | 39.2 | 1.3 |
| 34 | 67.4 | 30.9 | 0.5 |
| 35 | 70.1 | 26.0 | 2.1 |

The invention has been described in detail with particular reference to preferred embodiments thereof, but it will be understood that variations and modifications will be effected within the spirit and scope of the invention.

I claim:

1. Process for the preparation of a 3-alkyltetrahydrofuran having the formula

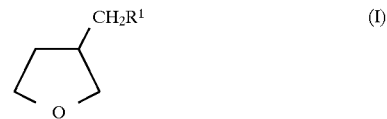

which comprises the steps of:
(1) contacting 2,3-dihydrofuran with an acetal having the formula

in the presence of an acidic catalyst to produce an intermediate compound having the formula

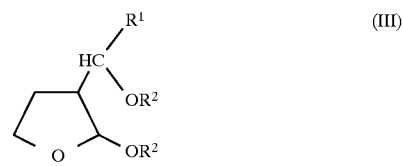

and
(2) contacting the intermediate compound from step (1) with hydrogen in the presence of a catalytic amount of a Group VIII noble metal or rhenium, water and a strong acid;
wherein $R^1$ is an aliphatic, cycloaliphatic, or aromatic radical of up to 12 carbon atoms and each $R^2$ is an alkyl radical of up to 12 carbon atoms.

2. Process according to claim 1 wherein step (1) is carried out at a temperature of about −20° to 50° C., the acidic catalyst is selected from Bronsted and Lewis acids and the acetal:2,3-dihydrofuran mole ratio is in the range of about 1:1 to 100:1 and step (2) is carried out at a temperature of about 150° to 350° C. and a hydrogen pressure of about 2 to 500 bars absolute in the presence of a Group VIII noble metal selected from palladium, platinum, rhodium, ruthenium and iridium.

3. Process according to claim 2 wherein step (2) is carried out in the presence of iodine or and iodine compound.

4. Process according to claim 2 wherein $R^1$ and each $R^2$ is independently selected from alkyl of up to about 8 carbon atoms.

5. Process for the preparation of a 3-alkyltetrahydrofuran having the formula

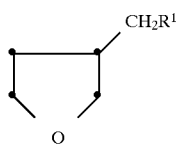

which comprises the steps of:

(1) contacting 2,3-dihydrofuran with an acetal having the formula

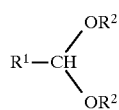

in the presence of an acidic catalyst selected from Bronsted and Lewis acids at a temperature of about −10° to 20° C. in an acetal:2,3-dihydrofuran mole ratio of about 3:1 to 10:1 to produce an intermediate compound having the formula

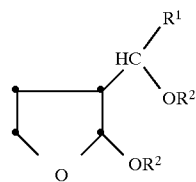

and (2) contacting the intermediate compound from step (1) with hydrogen in the presence of a catalytic amount of a Group VIII noble metal selected from palladium, rhodium and ruthenium, water and a strong acid selected from sulfuric, phosphoric and sulfonic acids at a temperature of about 150° to 350° C. and a hydrogen pressure of about 10 to 100 bars absolute;

wherein $R^1$ and each $R^2$ is independently selected from alkyl of up to about 8 carbon atoms.

6. Process according to claim 5 wherein step (2) is carried out in the presence of iodine or and iodine compound.

7. Process according to claim 5 wherein step (1) is carried out in the presence of an acidic catalyst selected from aluminum trichloride, aluminum tribromide, aluminum trifluoride, aluminum triiodide, boron trifluoride, boron trichloride, boron tribromide, boron triiodide, iron (III) chloride, iron (III) bromide, iron (III) fluoride, iron (III) iodide, tin (IV) chloride, tin (IV) bromide, tin (IV) fluoride, tin (IV) iodide, titanium (IV) fluoride, titanium (IV) chloride, titanium (IV) bromide, titanium (IV) iodide, zirconium tetrachloride, zirconium tetrabromide, zirconium tetrafluoride, zirconium tetraiodide, sulfuric acid, hydrogen chloride, hydrogen bromide, hydrogen iodide, hydrogen fluoride, phosphoric acid, trifluoroacetic acid, and toluenesulfonic acid.

8. Process according to claim 7 wherein step (1) is carried out in the presence of boron trifluoride, step (2) is carried out at a temperature of about 200° to 300° C. in the presence of a strong acid selected from sulfuric and phosphoric acids, wherein $R^1$ and each $R^2$ is independently selected from lower alkyl.

9. Process according to claim 8 wherein step (2) is carried out in the presence of a supported palladium catalyst.

* * * * *